(12) United States Patent
Seo et al.

(10) Patent No.: US 6,287,830 B1
(45) Date of Patent: Sep. 11, 2001

(54) FERMENTATION PROCESS FOR PREPARING ERYTHRITOL BY A HIGH SALT TOLERANT MUTANT OF CANDIDA SP.

(75) Inventors: Jin Ho Seo, Kyunggi-Do; Yeon Woo Ryu; Soo Ryun Jung, both of Seoul; Sang Yong Kim, Kyunggi-Do, all of (KR)

(73) Assignee: Bolak, Co., Ltd., Kyunggi-Do (KR)

( * ) Notice: Subject to any disclaimer, the term of this patent is extended or adjusted under 35 U.S.C. 154(b) by 0 days.

(21) Appl. No.: 09/344,609

(22) Filed: Jun. 25, 1999

(30) Foreign Application Priority Data

Jul. 20, 1998 (KR) .................................................. 98-29083

(51) Int. Cl.$^7$ ....................................................... C12P 7/18
(52) U.S. Cl. .................. 435/158; 435/254.1; 435/255.1; 435/255.21
(58) Field of Search ................................ 435/158, 254.1, 435/255.1, 255.21

(56) References Cited

U.S. PATENT DOCUMENTS 5,989,878 * 11/1999 Kim ...................................... 435/158

OTHER PUBLICATIONS

Spencer et al., Canad J Biochem, (1960 Feb.) 38 157–64.*
ATCC Catalogue of Yeasts, 1995, p. 16.*
Aoki et al., Biotech. Letters, 15(4):383–388, Apr. 1993.
Kwanabe et al., Basic Sciences, 26:358–362, 1992.
Hajny et al., Applied Microbiology, 12(3):240–246, May 1964.

* cited by examiner

Primary Examiner—Irene Marx
(74) Attorney, Agent, or Firm—Jacobson Holman, PLLC

(57) ABSTRACT

A fermentation process for preparing a high yield erythritol using a salt tolerant mutant of Candida sp. [*Candida magnoliae* SR101:KCCM-10160]. More specifically, the present invention relates to a process for preparing erytlritol under optimal fermentation conditions for maximal erythritol production by optimizing the environmental conditions of culture, including medium component, pH, temperature, aeration rate and agitation speed.

1 Claim, No Drawings

# FERMENTATION PROCESS FOR PREPARING ERYTHRITOL BY A HIGH SALT TOLERANT MUTANT OF CANDIDA SP.

BACKGROUND OF THE INVENTION

This application claims priority to Korean Patent Application Number 98-29083, filed Jul. 20, 1998, and the 98-29083 application is herein incorporated by this reference in its entirety.

1. Field of the Invention

The present invention relates to a fermentation process for preparing a high yield erythritol using a salt tolerant mutant of Candida sp. [*Candida magnoliae*, SR101:KCCM-10160]. More specifically, the present invention relates to a process for preparing erythritol under optimal fermentation conditions for maximal erythritol production by optimizing the environmental conditions of culture, including medium component, pH, temperature, aeration rate and agitation speed.

2. Background Art

Erythritol, a four carbon sugar alcohol, is a naturally occurring substance and is widely distributed in nature. Like most of the other polyols, it is a metabolite or storage compound for seaweeds and mushrooms. Fruits like melons, grapes and pears also contain erythritol. As it is often produced by bacteria, fungi, and yeasts, erythritol also occurs frequently in fermented food systems like wines or beers, and in processed vegetables, such as soy sauce or the oriental miso bean paste.

Erythritol is a moderately sweet bulking agent with 60–70 percent of the sweetness of sucrose in a ten percent solution. Its high positive enthalpy of solution provides the crystalline material with a strong cooling effect. As it has a taste which is very close to sucrose without bitter aftertaste, it is ideal to improve the taste of a combination with intense sweeteners like aspartame.

As a small molecule, erythritol also has strong colligative properties, i.e. a strong freezing point depression and boiling point elevation effect as well as a high osmotic pressure. In combination with its low hygroscopicity and viscosity in solution, it is also very useful to reduce and control the water activity of foodstuffs.

Erythritol produced from its natural sources, such as fruits and vegetables, occurs in relatively small amounts. Consequently, these natural sources are impractical for the high yield production of erythritol. Other methods of producing erythritol include chemical manipulation and the use of micro-organisms. Chemically, erythritol is produced by reduction of meso-tartarate, oxidation and reduction of 4,6-o-ethylidene-D-glucose, hydrolysis of dealdehyde starch, or addition of hydrogen. The production of erythritol by this and other related chemical processes, however, is expensive.

Erythritol produced by microbial methods is typically grown by use of osmophilic yeasts such as with species of the genus Torulopsis, such as *T. magnoliae, T. veratilis*, and *T candida; Endomycopsis chodati; Hansenula supelliculsa; Pichia miso; Monilliella tomentosa var. pollinis; Trigonopsis variabilis*; Trichosporonoides; *Candida zeylanoides*; and Aureobasidium. Some bacteria such as *Leuconostoc oenos* can also produce erythritol. *Monilliella toiiientosa var. pollinis* produced erythritol on a medium containing 35.7% glucose with 45.6% yield. Erythritol production using this strain did not apply to industrial scale due to by-products such as glycerol and ribitol. Industrial production of erythritol has been performed by a mutant of Aureobasidium. The mutant was isolated and developed by cooperative study of Nikken Chemical and National Research Institute of Japan. The mutant produced erythritol with 47.6% yield on a medium containing 22.5% glucose and 2 g/L-h volumetric productivity. However, the culture with this fungus had more difficultly than that with yeast.

The present invention presents a novel process for producing a high yield erythritol by isolating a wild yeast strain of Candida sp. from nature and mutating the yeast with EMS (Ethyl-methanol sulfonate) treatment. One of the mutants has superior properties to the wild strain in erythritol yield from glucose, volumetric productivity, and salt tolerance. By using the mutant of Candida sp., the optimization of the environmental conditions of culture was performed for maximal erythritol production.

SUMMARY OF THE INVENTION

The present invention provides novel mutants cells of *Candida magnoliae* SR101, which were deposited to Korean Culture Center of Microorganism 361-221, Yurim Building, Hongje-1-dong, Seodacmun-gu, Seoul 120-091, Korea with accession number KCCM-10160 on May 17, 1999 under Budapest treaty, which cells are used for preparing erythritol with high productivity.

The present invention also provides an optimal fermentation process for maximum production of erythritol using mutant cells of *Candida magnoliae* SR101 deposited to Korean Culture Center of Microorganism with accession number KCCM-10160 comprising the steps of:

a) fermenting monosaccharide or disaccharide medium with cells by controlling following fermentation conditions:
  i) composition of medium for maximum production of erythritol consists of 10–50 (w/v)% of glucose, 0.2–2.0 (w/v)% of yeast extract, 0.1–10 (w/v)% of $KH_2PO_4$, 0.1–5.0 (w/v)% of $(NH_4)_2SO_4$ and 0.01–1.0 (w/v)% of $MgSO_4.7H_2O$,
  ii) pH of culture medium is 6–8,
  iii) temperature of cultivation is 26–30° C.,
  iv) aeration rate is 0.75–2.0 volume of air per volume of medium per minute, and
  v) agitation speed is 300–1200 rpm;

b) feeding solution containing KCl continuously or intermittently fed into the culture broth during erythritol production phase to be 2–10% of its concentration;

c) removing cells from the fermentation medium; and d) separating and recovering erythritol from the fermentation medium of step c).

Various other objectives and advantages of the present invention will become apparent from the following description.

DETAILED DESCRIPTION OF THE INVENTION

As used in the claims, "a" can include multiples.

The present invention concerns a method for obtaining erythritol with a high yield and a high volumetric productivity using mutant cells of *Candida magnoliae* by optimizing culture conditions.

The mutant cells of the present invention are isolated by following method.

Candida sp. was screened from a comb. A piece of comb was transferred into the medium containing 40% of glucose and 1.0% of yeast extract, and incubated at 30° C. The broth was diluted and incubated at 30° C. on agar plate containing 20% of glucose, 1.0% of yeast extract and 2.0% of agar. After obtained colonies were incubated on fermentation medium, which consisted of 10% of glucose and 1.0% of yeast extract, the culture broth was centrifuged to remove cells, and the supernatant was analyzed for erythritol determination. A high erythritol producing strain was selected for erythritol production. The strain was identified to *Candida magnotiae* by the Microcheck Co.

The *Candida magnoliae* strain was incubated on growth medium containing 2.0% of glucose, 1.0% of yeast extract and 1.0% of peptone. After growth, the broth was spread on an agar plate containing 10% of glucose, 0.8% of yeast extract, 0.3% of peptone and 2.0% of agar, and the obtained colony was transferred on sporulation medium containing 0.1% of glucose, 1.0% of yeast extract and 2.0% of agar. The formed spore was harvested by autoclaved distilled water and was selected by adding 10 mM of 2-mercaptoethanol for 30 minutes and treating with lyticase 0.5 mg/ml for 4 hours.

The selected spore was treated by EMS (ethylmethanol sulfonate), and was incubated on the medium containing 30% of glucose, 18% of KCl, 0.1% of yeast extract and 2.0% of agar. Single colony was selected as fast growing mutants for the selection of a high salt tolerant mutant. The selected colony was transferred on the fermentation medium to test erythritol producing activity in shake flask.

After incubating at 30° C. and 240 rpm for 72 hours, a high erythritol producing mutant was selected. Finally, growing colony was isolated and obtained as mutant cells, and used as a producing strain in this invention. These mutant cells were deposited to Korean Culture Center of Microorganisms 361-221, Yurim Building, Hongie-1-dong, Seodaemun-gu, Seoul 120-091, Korea with accession number KCCM-10160 on May 17, 1999 under Budapest treaty.

The following is fermentation method for producing erythritol using mutants cells.

Seed Culture

The cells of *Candida magnoliae* [KCCM-10160] are cultivated in a 250-mL flask containing 40–60 mL of growth medium (2.0% of glucose, 1.0% of peptone, 1.0% of yeast extract) at 30° C. and 240 rpm for 48 hours and the seed culture was transferred to a 250-ml flask or a 5-L fermentor for producing erythritol in a main culture.

Main Culture

Flask experiments with fermentation medium were performed at 26–30° C. and 300–1200 rpm in 60–100 hours. The fermentation medium consisted of 10–50% of glucose as carbon source and 0.2–2.0% of yeast extract, 0.1–15.0% of $(NH_4)SO_4$, 0.1–10% of $KH_2PO_4$ and 0.01–1.0% of $Mg_2SO_4.7H_2O$ were used to be inorganic sources. For the experimental purpose, glucose concentration was adjusted. Batch and fed-batch culture in the fermentor were performed at 26–30° C. and initial pH 7. Aeration rate was in the range of 0.75–2.0 vvm. Agitation speed was 300–1200 rpm. Fed-batch culture was performed with 5–10% of glucose by adding continuously or intermittently 10–40% of glucose.

The fermentation process is preferably by fed-batch process. After glucose was completely consumed in the medium, the amount of erythritol is measured by high performance liquid chromatography equipped with Carbohydrate Analysis column. Dry cell weight is estimated by using a calibration curve made from relationship between optical density at 600 nm and dry cell weight. Glucose is measured by dinitrosalicylic acid method.

The measured yield of erythritol is 35–55% of glucose consumption and volumetric productivity is 0.7 g/L-h.

Finally the fermentation medium is centrifuged for removing cells and other residue, and the supernatant is filtered and dialyzed for obtaining erythritol.

The present invention is more particularly described in the following examples which are intended as illustrative only since numerous modifications and can be explained more specifically by following examples.

EXAMPLES

Example I

Isolation of Mutant Cells

Canclia sp. was screened from a comb. A piece of comb was transferred into the medium containing 40% of glucose and 1.0% of yeast extract and incubated at 30° C. The broth was diluted and incubated at 30° C. on agar plate containing 20% of glucose, 1.0% of yeast extract and 2.0% of agar. After obtained colonies were incubated on fermentation medium, which consisted of 10% of glucose and 1.0% of yeast extract, the culture broth was centrifuged to remove cells and the supernant was analyzed for erythritol determination. A high erythritol producing strain was selected for erythritol production. The strain was identified to *Candida magnoliae* by Microcheck Co.

This strain was incubated at 30° C. for 48 hours on growth medium containing 2.0% of glucose, 1.0% of yeast extract and 1.0% of peptone. After growth, the broth was spread on agar plate containing 10% of glucose, 0.8% of yeast extract, 0.3% of peptone and 2.0% of agar at 30° C. for 36 hours, and then obtained colony was transferrred on sporulation medium containing 0.1% of glucose, 1.0% of yeast extract and 2.0% of agar, and spores were formed at 4° C. after 4 days. The formed spore was harvested by autoclaved distilled water and was selected by adding 10 mM of 2-mercaptoethanol for 30 minutes and treating with lyticase 0.5 mg/ml (100,000 units) for 4 hours. The selected spore was treated for 30 minutes by EMS. The reaction was terminated by adding 5% of thiosulfate. The spore was incubated on the medium containing 30% of glucose, 18% of KCl, 0.1% of yeast extract and 2.0% of agar for the selection of a high salt tolerant mutant. Single colony was selected as fast growing mutants. The selected colonies were transferred on the fermentation medium of 50 mL to test erythritol producing activity in 250 mL-shake flask. After incubating at 30° C. and 240 rpm in 72 hours, a high erythritol producing mutant was selected. Finally, growing colony was isolated and obtained as mutant cells and used as a producing strain in this invention. These mutant cells were deposited to Korean Culture Center of Microorganism with accession number KCCM-10160.

Example II

Erythritol Production by the Fermentation of Mutant Cells

The mutant cells of *Candida magnoliae* [KCCM-10160] are cultivated in a 250 mL flask containing 50 mL of growth medium (2.0% of glucose, 1.0% of peptone, 1.0% of yeast extract) at 30° C. and 240 rpm for 48 hours and this seed culture was transferred to a 250-ml flask for producing erythritol. Flask experiments with fermentation medium were performed at 280° C., initial pH 7, and 240 rpm for 84 hours. The fermentation medium consisted of 25% of glucose as carbon source and 0.5% of yeast extract, 0.2% of $(NH_4)_2SO_4$, 0.5% of $KH_2PO_4$ and 0.04% of $MgSO.7H_2O$.

After 84 hours fermentation, the amount of erythritol from 10% of glucose is measured by HPLC equipped with Carbohydrate Analysis column. The obtained erythritol is 25 g/L and volumetric productivity is 0.30 g/L-h.

Comparative Example I
Erythritol Production by the Fermentation of Wild Type of Cells The wild type of cells of *Candida magnoliae* are cultivated in a 250-mL flask containing 50 mL of growth medium (2.0% of glucose, 1.0% of peptone, 1.0% of yeast extract) at 30° C. and 240 rpm for 48 hours, and this seed culture was transferred to a 250-ml flask for producing erythritol. Flask experiments with fermentation medium were performed at 28° C., initial pH 7, and 240 rpm for 108 hours. The fermentation medium consisted of 25% of glucose as carbon source and 0.5% of yeast extract, 0.2% of $(NH_4)_2SO_4$, 0.5% of $KH_2PO_4$ and 0.04% of $MgSO_4.7H_2O$.

After 108 hours fermentation, the amount of erythritol from 10% of glucose is measured by HPLC equipped with Carbohydrate Analysis column. The obtained erythritol is 17 g/L and volumetric productivity is 0.16 g/L-h.

Example III
The Effect of Initial pH for Erythritol Production

The mutant cells of *Candida magnoliae* [KCCM-10160] are cultivated in a 250-mL flask containing 50 mL of growth medium (2.0% of glucose, 1.0% of peptone, 1.0% of yeast extract) at 300° C. and 240 rpm for 48 hours, and this seed culture was transferred to a 250-ml flask for producing erythritol. Flask experiments with fermentation medium were performed at 280° C. and 240 rpm for 84 hours. The fermentation medium consisted of 25% of glucose as carbon source and 0.5% of yeast extract, 0.2% of $(NH_4)_2SO_4$, 0.5% of $KH_2PO_4$ and 0.04% of $MgSO_4.7H_2O$. Effect of pH on erythritol production was investigated.

After 84 hours fermentation, the amount of erythritol at initial pH of 5.0 is measured by HPLC equipped with Carbohydrate Analysis column. The obtained erythritol is 21.4 g/L and volumetric productivity is 0.25 g/L-h.

After 84 hours fermentation, the amount of erythritol at initial pH of 6.0 is measured by HPLC equipped with Carbohydrate Analysis column. The obtained erythritol is 23.6 g/L and volumetric productivity is 0.28 g/L-h.

After 84 hours fermentation, the amount of erythritol at initial pH of 7.0 is measured by HPLC equipped with Carbohydrate Analysis column. The obtained erythritol is 25.0 g/L and volumetric productivity is 0.30 g/L-h.

After 84 hours fermentation, the amount of erythritol at initial pH of 5.0 is measured by HPLC equipped with Carbohydrate Analysis column. The obtained erythritol is 18.6 g/L and volumetric productivity is 0.22 g/L-h.

Example IV
The Effect of Temperature for Erythritol Production

The mutant cells of *Candida magnoliae* [KCCM-10160] are cultivated in a 250-ml, flask containing 50 mL of growth medium (2.0% of glucose, 1.0% of peptone, 1.0% of yeast extract) at 30° C. and 240 rpm for 48 hours, and this seed culture was transferred to a 250-ml flask for producing erythritol. Flask experiments with fermentation medium were performed at initial pH of 7.0 and 240 rpm for 84 hours. The fermentation medium consisted of 25% of glucose as carbon source and 0.5% of yeast extract, 0.2% of $(NH_4)_2SO_4$, 0.5 % of $KH_2PO_4$ and 0.04% of $MgSO_4.7H_2O$. Effect of temperature on erythritol production was investigated.

After 84 hours fermentation, the amount of erythritol at 26° C. is measured by HPLC equipped with Carbohydrate Analysis column. The obtained erythritol is 15.0 g/L and volumetric productivity is 0.18 g/L-h.

After 84 hours fermentation, the amount of erythritol at 28° C. is measured by HPLC equipped with Carbohydrate Analysis column. The obtained erythritol is 25.0 g/L and volumetric productivity is 0.30 g/L-h.

After 84 hours fermentation, the amount of erythritol at 30° C. is measured by HPLC equipped with Carbohydrate Analysis column. The obtained erythritol is 20.7 g/L and volumetric productivity is 0.25 g/L-h.

Example V
The Effect of the KCl Concentration for Erythritol Production

The mutant cells of *Candida magnoliae* [KCCM-10160] are cultivated in a 250-mL flask containing 50 mL of growth medium (2.0% of glucose, 1.0% of peptone, 1.0% of yeast extract) at 30° C. and 240 rpm for 48 hours, and this seed culture was transferred to a 250-ml flask for producing erythritol. Flask experiments with fermentation medium were performed at 280° C. and 240 rpm for 84 hours. The fermentation medium consisted of 25% of glucose as carbon source and 0.5% of yeast extract, 0.2% of $(NH_4)_2SO_4$, 0.5% of $KH_2PO_4$ and 0.04% of $MgSO_4.7H_2O$. Effect of KCl concentration on erythritol production was investigated.

After 84 hours fermentation, the amount of erythritol at 0.0% KCl is measured by HPLC equipped with Carbohydrate Analysis column. The obtained erythritol is 25.0 g/L and volumetric productivity is 0.30 g/L-h.

After 84 hours fermentation, the amount of erythritol at 1.0% KCl is measured by HPLC equipped with Carbohydrate Analysis column. The obtained erythritol is 25.2 g/L and volumetric productivity is 0.30 g/L-h.

After 84 hours fermentation, the amount of erythritol at 3.0% KCl is measured by HPLC equipped with Carbohydrate Analysis column. The obtained erythritol is 23.3 g/L and volumetric productivity is 0.28 g/L-h.

After 84 hours fermentation, the amount of erythritol at 5.0% KCl is measured by HPLC equipped with Carbohydrate Analysis column. The obtained erythritol is 27.6 g/L and volumetric productivity is 0.33 g/L-h.

After 84 hours fermentation, the amount of erythritol at 6.0% KCl is measured by HPLC equipped with Carbohydrate Analysis column. The obtained erythritol is 26.5 g/L and volumetric productivity is 0.32 g/L-h.

Comparative Example II
The Effect of the KCl Concentration for Erythritol Production Using Wild Type of Cells.

The wild type of cells of *Candida magnoliae* are cultivated in a 250-mL flask containing 50 mL of growth medium (2.0% of glucose, 1.0% of peptone, 1.0% of yeast extract) at 30° C. and 240 rpm for 48 hours, and this seed culture was transferred to a 250-n-d flask for producing erythritol. Flask experiments with fermentation medium were performed at 280° C. and 240 rpm for 108 hours. The fermentation medium consisted of 25% of glucose as carbon source and 0.5% of yeast extract, 0.2% of $(NH_4)_2SO_4$, 0.5% of $KH_2PO_4$ and 0.04% of $MgSO_4.7H_2O$. Effect of KCl concentration on erythritol production was investigated.

After 84 hours fermentation, the amount of erythritol at 0.0% KCl is measured by HPLC equipped with Carbohydrate Analysis column. The obtained erythritol is 17.0 g/L and volumetric productivity is 0.16 g/L-h.

After 108 hours fermentation, the amount of erythritol at 1.0% KCl is measured by HPLC equipped with Carbohydrate Analysis column. The obtained erythritol is 24.0 g/L and volumetric productivity is 0.22 g/L-h.

After 108 hours fermentation, the amount of erythritol at 2.0% KCl is measured by HPLC equipped with Carbohydrate Analysis column. The obtained erythritol is 23.7 g/L and volumetric productivity is 0.26 g/L-h.

After 108 hours fermentation, the amount of erythritol at 3.0% KCl is measured by HPLC equipped with Carbohydrate Analysis column. The obtained erythritol is 14.2 g/L and volumetric productivity is 0.13 g/L-h.

Example VI
The Erythritol Production According to the Change of Aeration n the Fermentor The mutant cells of *Candida magnoliae* [KCCM-10160] are cultivated in a 250-mL flask containing 50 mL of growth medium (2.0% of glucose, 1.0% of peptone, 1.0% of yeast extract) at 30° C. and 240 rpm for 48 hours, and this seed culture was transferred to a 5-L, fermentor for producing erythritol. Fermentor experiments with fermentation medium were performed at 28° C., initial pH of 7.0, and 500 rpm. The fermentation medium consisted of 25% of glucose as carbon source and 0.5% of yeast extract, 0.2% of $(NH_4)_2SO_4$, 0.5% of $KH_2PO_4$ and 0.04% of $MgSO_4.7H_2O$. Effect of aeration rate on erythritol production was investigated.

After 205 hours fermentation, the amount of erythritol at 0.75 vvm is measured by HPLC equipped with Carbohydrate Analysis column. The obtained erythritol is 131.2 g/L and volumetric productivity is 0.64 g/L-h.

After 205 hours fermentation, the amount of erythritol at 1.00 vvm is measured by HPLC equipped with Carbohydrate Analysis column. The obtained erythritol is 143.3 gIL and volumetric productivity is 0.70 g/L-h.

After 205 hours fermentation, the amount of erythritol at 1.50 vvm is measured by HPLC equipped with Carbohydrate Analysis column. The obtained erythritol is 125.0 g/L and volumetric productivity is 0.61 g/L-h.

Example VII
The Ervthritol Production According to the Change of Glucose Concentration in the Fermentor The mutant cells of *Candida magnoliae* [KCCM-10160] are cultivated in a 250-mL flask containing 50 mL of growth medium (2.0% of glucose, 1.0% of peptone, 1.0% of yeast extract) at 300° C. and 240 rpm for 48 hours, and this seed culture was transferred to a 5-L fermentor for producing erythritol. Fermentor experiments with fermentation medium were performed at 28° C., initial pH of 7.0, 1.0 vvm, and 500 rpm for 84 hours. The fermentation medium consisted of glucose as carbon source and 0.5% of yeast extract, 0.2% of $(NH_4)_2SO_4$, 0.5% of $KH_2PO_4$, 5.0% of KCl and 0.04% Of $MgSO_4.7H_2O$. Effect of glucose concentration on erythritol production was investigated.

After 63 hours fermentation, the amount of erythritol at 10% of glucose is measured by HPLC equipped with Carbohydrate Analysis column. The obtained erythritol is 29.1 g/L and volumetric productivity is 0.46 g/L-h.

After 120 hours fermentation, the amount of erythritol at 15% of glucose is measured by HPLC equipped with Carbohydrate Analysis column. The obtained erythritol is 64.9 g/L and volumetric productivity is 0.54 g/L-h.

After 160 hours fermentation, the amount of erythritol at 20% of glucose is measured by HPLC equipped with Carbohydrate Analysis column. The obtained erythritol is 87.2 g/L and volumetric productivity is 0.55 g/L-h.

After 205 hours fermentation, the amount of erythritol at 25% of glucose is measured by HPLC equipped with Carbohydrate Analysis column. The obtained erythritol is 143 g/L and volumetric productivity is 0.70 g/L-h.

After 205 hours fermentation, the amount of erythritol at 30% of glucose is measured by HPLC equipped with Carbohydrate Analysis column. The obtained erythritol is 117 g/L and volumetric productivity is 0.57 g/L-h.

Example VIII
The Erythritol Production According to the Change of Sucrose Concentration in the Fermentor The mutant cells of *Candida magnoliae* [KCCM-10160] are cultivated in a 250-mL flask containing 50 mL of growth medium (2.0% of glucose, 1.0% of peptone, 1.0% of yeast extract) at 30° C. and 240 rpm for 48 hours, and this seed culture was transferred to a 5-L fermentor for producing erythritol. Fermentor experiments with fermentation medium were performed at 28° C., initial pH of 7.0, 1.0 vvm, and 500 rpm for 84 hours. The fermentation medium consisted of sucrose as carbon source and 0.5% of yeast extract, 0.2% of $(NH_4)_2SO_4$, 0.5% of $KH_2PO_4$, 5.0% of KCl, and 0.04% of $MgSO_4.7H_2O$. Effect of sucrose concentration on erythritol production was investigated.

After 65 hours fermentation, the amount of elytiritol at 10% of sucrose is measured by HPLC equipped with Carbohydrate Analysis column. The obtained erythritol is 26.1 g/L and volumetric productivity is 0.40 g/L-h.

After 154 hours fermentation, the amount of erythritol at 20% of sucrose is measured by HPLC equipped with Carbohydrate Analysis column. The obtained erythritol is 78.3 g/L and volumetric productivity is 0.51 g/L-h.

After 175 hours fermentation, the amount of erythritol at 20% of sucrose is measured by HPLC equipped with Carbohydrate Analysis column. The obtained erythritol is 105 g/L and volumetric productivity is 0.60 g/L-h.

After 250 hours fermentation, the amount of erythritol at 40% sucrose is measured by HPLC equipped with Carbohydrate Analysis column. The obtained erythritol is 126 g/L and volumetric productivity is 0.50 g/L-h.

*Candida magnoliae* [KCCM-10160] in the present can produce erythritol from glucose or sucrose with a high productivity and a high yield, make little foam, and does not produce by-products such as glyccerol, resulting in easy recovery. These advantages have considerable importance for the possible commercial manufacture of erythritol.

We claim:

1. A fermentation process for the production of erythritol using cells of *Candida magnoliae* SR101 deposited to Korean Culture Center of Microorganism with accession number KCCM-10160 comprising:

a) fermenting glucose medium with cells of *Candida magnoliae* SR202 deposited to Korean Culture Center of Microorganism;

b) feeding a solution containing KCl continuously or intermittently into the culture broth during erythritol production phase to maintain 2–10 (w/v) % of KCl concentration in the culture broth;

c) removing the cells from the fermentation medium; and d) separating and recovering erythritol from the fermentation medium of step c), wherein the conditions for fermenting glucose medium are:
   i) medium composition consisting of 10–50 (w/v) % of glucose, 0.2–2.0 (w/v) % of yeast extract, 0.1–10 (w/v) % of $KH_2PO_4$, 0.1–5.0 (w/v) % of $(NH_4)_2SO_4$ and 0.01–1.0 (w/v) % of $MgSO_4.7H2O$,
   ii) pH of culture medium is 6.0–8.0,
   iii) temperature of cultivation is 26–30° C.,
   iv) aeration rate is 0.75–2.0 volume of air per volume of medium per minute, and
   v) agitation speed is 300–1200 rpm.

* * * * *